(12) United States Patent
Schoenle et al.

(10) Patent No.: US 10,307,580 B2
(45) Date of Patent: Jun. 4, 2019

(54) DEVICES, SYSTEMS AND METHODS FOR ENHANCING INTRALUMINAL DRUG DELIVERY AND UPTAKE

(71) Applicant: Cardiovascular Systems, Inc., St. Paul, MN (US)

(72) Inventors: Victor L. Schoenle, Greenfield, MN (US); Matthew D. Cambronne, North Oaks, MN (US); Brittany N. Pusey, Minneapolis, MN (US); Jeffrey A. McBroom, Champlin, MN (US)

(73) Assignee: Cardiovascular Systems, Inc., New Brighton, MN (US)

( * ) Notice: Subject to any disclaimer, the term of this patent is extended or adjusted under 35 U.S.C. 154(b) by 171 days.

(21) Appl. No.: 15/190,730

(22) Filed: Jun. 23, 2016

(65) Prior Publication Data
US 2016/0375235 A1 Dec. 29, 2016

Related U.S. Application Data

(60) Provisional application No. 62/184,434, filed on Jun. 25, 2015, provisional application No. 62/190,910, filed on Jul. 10, 2015.

(51) Int. Cl.
*A61M 37/00* (2006.01)
*A61B 17/3207* (2006.01)
(Continued)

(52) U.S. Cl.
CPC . *A61M 37/0092* (2013.01); *A61B 17/320758* (2013.01); *A61K 41/0023* (2013.01); *A61B 2017/22065* (2013.01); *A61B 2017/22084* (2013.01); *A61B 2017/22088* (2013.01); *A61B 2017/320004* (2013.01); *A61B 2017/320766* (2013.01); *A61M 2025/105* (2013.01); *A61M 2230/04* (2013.01)

(58) Field of Classification Search
CPC .......... A61B 2017/22065; A61B 2017/22088; A61M 2025/105; A61M 2230/04; A61M 37/0092
See application file for complete search history.

(56) References Cited

U.S. PATENT DOCUMENTS 6,484,052 B1 11/2002 Visuri et al.
2004/0229830 A1 11/2004 Tachibana
(Continued)

OTHER PUBLICATIONS

PCT International Preliminary Report on Patentability, dated Dec. 26, 2017, for PCT Application No. PCT/US2016/039228, filed on Jun. 24, 2016.
(Continued)

*Primary Examiner* — Deanna K Hall
(74) *Attorney, Agent, or Firm* — Barnes & Thornburg LLP; Jeffrey Stone

(57) ABSTRACT

The present disclosure generally relates to methods, devices and systems relating to applying drugs or therapeutic agents to biological conduits, e.g., vascular lumens. More specifically, the present invention comprises enhancing the uptake of drugs or therapeutic agents encapsulated in microbubbles in combination with ultrasound energy as well as applying drugs or therapeutic agents in a cyclic manner using a pulse generator that may be matched in frequency with a patient's blood pulsing.

7 Claims, 8 Drawing Sheets

(51) Int. Cl.
*A61K 41/00* (2006.01)
*A61M 25/10* (2013.01)
*A61B 17/22* (2006.01)
*A61B 17/32* (2006.01)

(56) References Cited

U.S. PATENT DOCUMENTS

| | | |
|---|---|---|
| 2007/0142770 A1 | 6/2007 | Rioux et al. |
| 2011/0202079 A1 | 8/2011 | Schoenle et al. |
| 2012/0259401 A1* | 10/2012 | Gerrans .................. A61F 2/958 623/1.11 |
| 2013/0023802 A1 | 1/2013 | McIntosh et al. |
| 2014/0039358 A1 | 2/2014 | Zhou et al. |

OTHER PUBLICATIONS

Extended European Search Report, dated Feb. 12, 2019, for PCT Application No. PCT/US2016/039228.

* cited by examiner

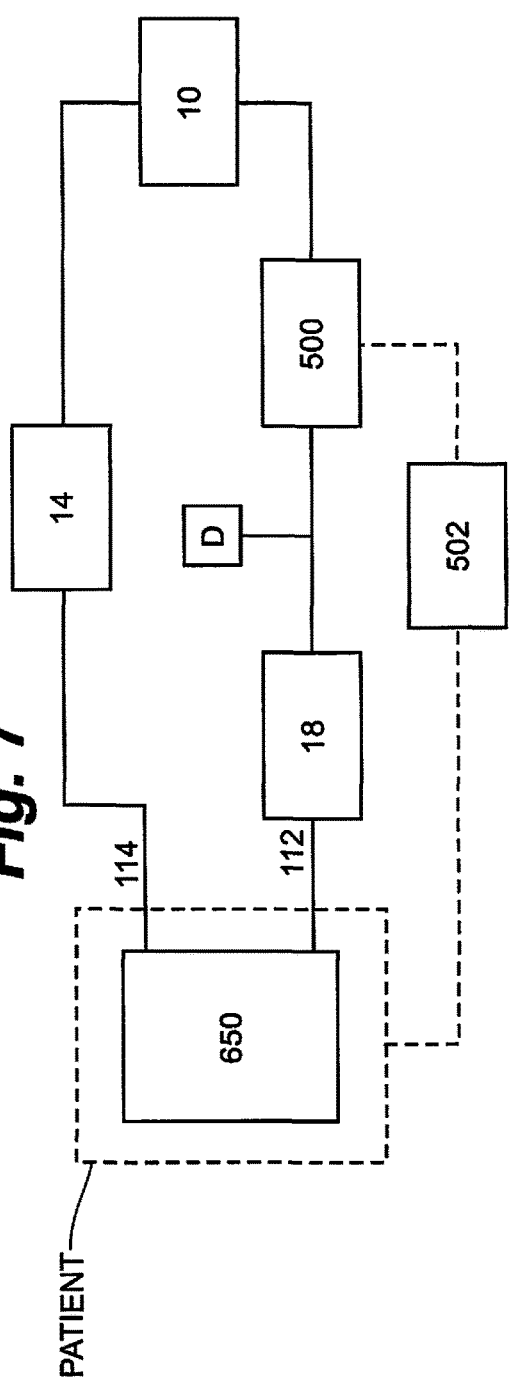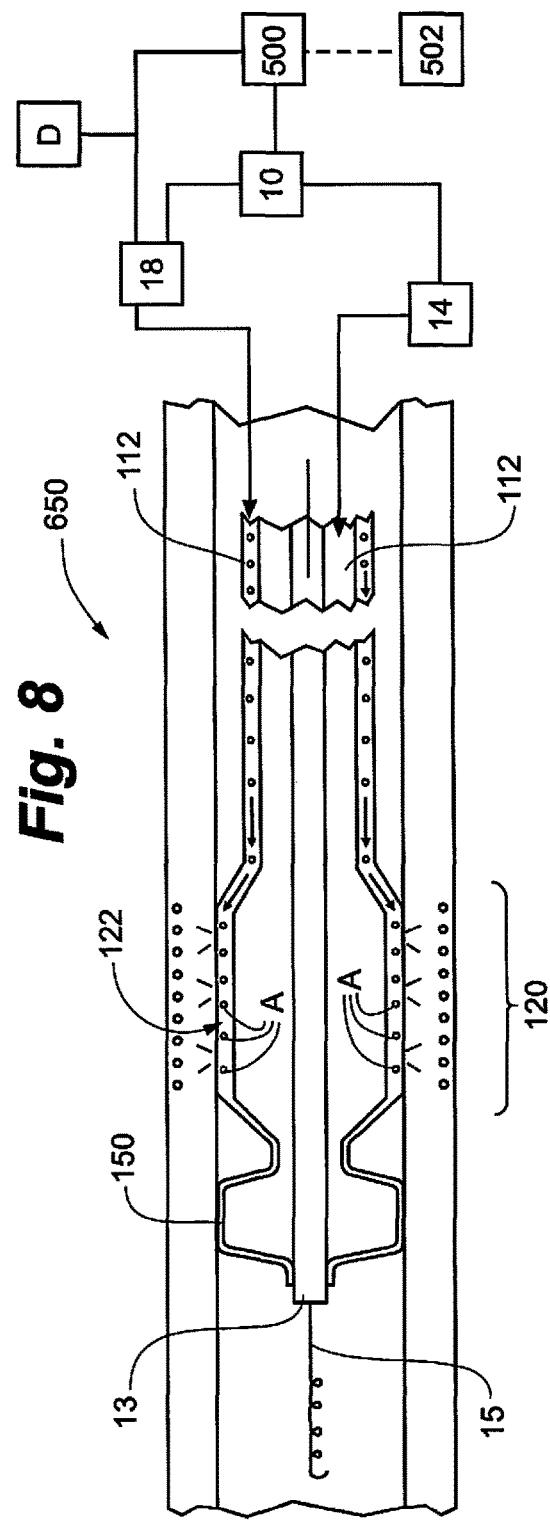

DEVICES, SYSTEMS AND METHODS FOR ENHANCING INTRALUMINAL DRUG DELIVERY AND UPTAKE

CROSS-REFERENCE TO RELATED APPLICATIONS

This application claims the benefit of U.S. Provisional Application No. 62/184,434 filed on Jun. 25, 2015 entitled "Devices, Systems and Methods for Improving Intraluminal Drug Delivery"; and claims the benefit of U.S. Provisional Application 62/190,910 filed on Jul. 10, 2015 entitled "Device, Systems and Methods for Enhancing Vasculature Drug Uptake With Microbubbles and Ultrasound", the entire contents of each of which are hereby incorporated by reference.

FIELD OF THE INVENTION

The present disclosure generally relates to methods, devices and systems relating to applying drugs or therapeutic agents to biological lumens, e.g., vascular lumens. More specifically, the present invention comprises enhancing the uptake of drugs or therapeutic agents encapsulated in microbubbles in combination with ultrasound energy as well as applying drugs or therapeutic agents in a cyclic manner using a pulse generator.

BACKGROUND OF THE INVENTION

Several kinds of rotational atherectomy devices have been developed for attempting to remove stenotic material. For example, U.S. Pat. No. 6,494,890 (Shturman) discloses an atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. The disclosure of U.S. Pat. No. 6,494,890 is hereby incorporated by reference in its entirety.

No matter the technique used to open an occluded conduit, e.g., blood vessel, and restore normal fluid flow therethrough, one problem remains: restenosis. A certain percentage of the treated conduits and vessels will re-occlude (restenose) after a period of time; occurring in as many as 30-40% of the cases. When restenosis does occur, the original procedure may be repeated or an alternative method may be used to reestablish fluid, e.g., blood, flow.

The relevant commonality shared by each of the above treatment methods is that each one results in some trauma to the conduit wall. Restenosis occurs for a variety of reasons; each involving trauma. Small clots may form on the arterial wall. Small tears in the wall expose the blood to foreign material and proteins which are highly thrombogenic. Resulting clots may grow gradually and may even contain growth hormones released by platelets within the clot. Moreover, growth hormones released by other cells, e.g., macrophages, may cause smooth muscle cells and fibroblasts in the affected region to multiply in an abnormal fashion. There may be an injury in the conduit wall due to the above methods that results in inflammation which may result in the growth of new tissue.

It is known that certain therapeutic substances may have a positive effect on prevention and/or inhibition of restenosis. Several difficulties present themselves in the application of these substances to the affected region in a therapeutic dose. For example, the region in need of treatment is very small and localized. Fluid, e.g., blood, flow in the conduit is continuous, resulting in a flow boundary along the wall which must be disrupted so that the therapeutic substances may reach the localized region of interest within a dose range considered therapeutic. The art fails to adequately provide a mechanism for breaking through this flow boundary to target the region of interest; electing instead generally to place the therapeutic substance into the general flow of the conduit, either by intravenous means or intra-lumen infusion, at a dose that is much higher than therapeutic since the majority of the therapeutic substance will simply flow downstream and either be absorbed systemically or eliminated as waste. For example, intravenous medications are delivered systemically by vein, or regionally, e.g., through intra-lumen infusion without targeting the subject region. Such unnecessary systemic exposure results with unknown and unnecessary adverse results in regions, tissue, and/or organs that are distant from the region of interest. Clearly, systemic delivery and exposure is not well suited to treatment of diseases or conditions having a single intra-lumen region of interest.

The potential utility of localized application of a therapeutic dose of therapeutic substances is not limited to treatment of coronary arteries. Beyond coronary artery delivery, other sites of atherosclerosis, e.g., renal, iliac, femoral, distal leg and carotid arteries, as well as saphenous vein grafts, synthetic grafts and arterio-venous shunts used for hemodialysis would be appropriate biological conduits for a localized therapeutic substance delivery method and mechanism. Nor is the potential utility limited to blood vessels; any biological conduit having a region of interest amenable to treatment may benefit from such a treatment method and mechanism.

Generally, when introducing a drug and/or therapeutic agent to the lumen wall, known drug delivery systems rely on stopping the blood flow in the region of interest or making physical contact with the lumen wall. In the former case, the endothelial tissue and cells in the region of interest are under tension from the occluding portions of the balloon. In the latter case, the endothelial tissue and cells in the region of interest are under constant pressure from the injection pressure required to inject the drug or agent through the flowing fluid for application at the lumen wall. Both known systems and methods pressurize and elongate the endothelial cells and tissue, creating less than optimal conditions for the cells to absorb the drug or agent.

In addition, drug coated balloons suffer from a very low uptake of the drug or agent coated on the balloon's exterior surface. Further, a large amount of the drug or agent is simply sloughed off of the balloon and, therefore, are exposed to the subject patient's system and non-target organs. Because of these issues, a much larger than therapeutic dose of the drug or agent must be applied to the balloon, in hopes that a therapeutic amount will actually be taken up by the cells in the region of interest. Unfortunately, the patient's system and non-target organs are exposed to unwanted drugs or agents.

Various embodiments of the present invention address these problems.

BRIEF SUMMARY OF THE INVENTION

The present disclosure generally relates to methods, devices and systems relating to applying drugs or therapeutic agents to biological conduits, e.g., vascular lumens. More specifically, the present invention comprises enhancing the uptake of drugs or therapeutic agents encapsulated in microbubbles in combination with ultrasound energy as well as applying drugs or therapeutic agents in a cyclic manner using a pulse generator that may be matched in frequency with a patient's blood pulsing.

To improve uptake of drugs or agents to the tissue and cells within vascular lumen walls, the drugs and/or agents may be delivered to the region of interest, i.e., the tissue and/or cells within a vascular lumen such as an artery, various embodiments of the present invention combine encasing of the drug and/or agent within microbubbles, the process for such encasement is well known in the art, with ultrasound energy. Generally, this process is known as sonoporation which, in various embodiments of the present invention, comprises the inventive use of ultrasonic sound frequencies to modify the permeability of the cell plasma membrane in the region of interest in order to allow uptake of molecules. Sonoporation causes vibration and/or acoustic cavitation of microbubbles to enhance delivery of the encapsulated drugs or agent by (1) forming pores in the target cell wall; (2) endocytosis; and/or (3) openings in the cell-cell junctions, all of which make it easier for the administered drug to enter cells at the target region of interest.

With the use of microbubble-encased drugs and/or agents, and ultrasound, the uptake of the encapsulated drug and/or agent into the tissue or cells within the region of interest is enhanced. This results in a greater efficiency of drug or agent delivery to the target tissue and/or cells which, in turn, requires a smaller, and less expensive, dose of the drug and/or agent to be administered in order to achieve a therapeutically effective amount applied, and taken up, at the region of interest.

In addition, and as a result, sonoporation protects the subject patient's system and non-target organs from unwanted exposure to the drug and/or agent by (1) the reduction of administered dose that is required; and (2) encapsulation of the drug and/or agent in microbubbles, so that if the encapsulated drug and/or agent is not actually delivered to the target tissue and/or cells, and if the encapsulating microbubble does not burst due to the ultrasonic energy being applied, the encapsulated drug and/or agent is cleared from the body without any non-target exposure.

An alternative to the use of ultrasound energy is to administer the drug and/or agent with a cyclic pulsatile pressure force that may, in some embodiments, be synced with the subject patient's natural blood pulses. In the synced embodiment, the cells in the target region of the lumen wall will experience the same mechanical forces and biological effects that the blood vessel, e.g., artery, experiences while promoting enhanced uptake of the administered drug and/or agent. Alternatively, the frequency of the pulsatile pressure force may be increased to mimic the patient's cardiac output at full exertion, or perhaps higher than full exertion which may, inter alia, reduce the time needed to take up a therapeutically effective amount of the administered drug and/or agent. In other embodiments, a range of pulsatile pressure force frequencies may be provided.

BRIEF DESCRIPTION OF THE DRAWINGS

FIG. 7 illustrates a schematic view of one embodiment of the present invention.

FIG. 8 illustrates a side cutaway and schematic view of one embodiment of the present invention.

DETAILED DESCRIPTION

Figure 1A:
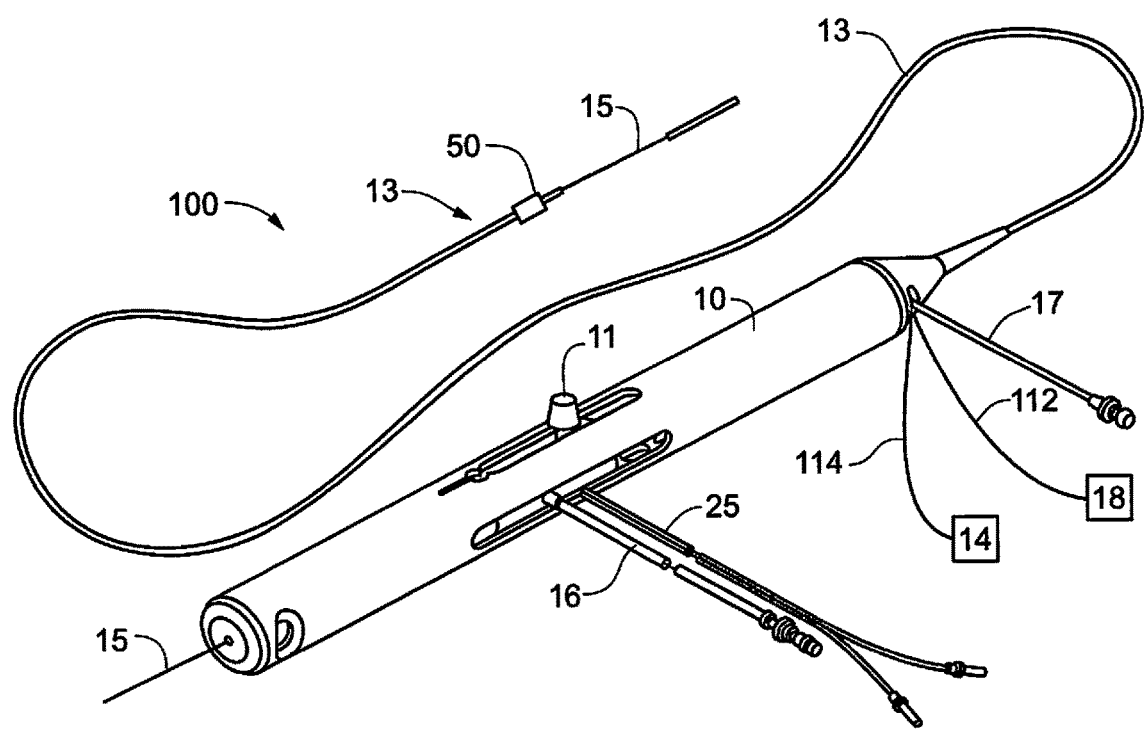
FIG. 1A illustrates a perspective view of one embodiment of the present invention.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

Various embodiments of the present invention may be incorporated into a rotational atherectomy system as described generally in U.S. Pat. No. 6,494,890, entitled "ECCENTRIC ROTATIONAL ATHERECTOMY DEVICE," which is incorporated herein by reference. Additionally, the disclosure of the following co-owned patents or patent applications are herein incorporated by reference in their entireties: U.S. Pat. No. 6,295,712, entitled "ROTATIONAL ATHERECTOMY DEVICE"; U.S. Pat. No. 6,132,444, entitled "ECCENTRIC DRIVE SHAFT FOR ATHERECTOMY DEVICE AND METHOD FOR MANUFACTURE"; U.S. Pat. No. 6,638,288, entitled "ECCENTRIC DRIVE SHAFT FOR ATHERECTOMY DEVICE AND METHOD FOR MANUFACTURE"; U.S. Pat. No. 5,314,438, entitled "ABRASIVE DRIVE SHAFT DEVICE FOR ROTATIONAL ATHERECTOMY"; U.S. Pat. No. 6,217,595, entitled "ROTATIONAL ATHERECTOMY DEVICE"; U.S. Pat. No. 5,554,163, entitled "ATHERECTOMY DEVICE"; U.S. Pat. No. 7,507,245, entitled "ROTATIONAL ANGIOPLASTY DEVICE WITH ABRASIVE CROWN"; U.S. Pat. No. 6,129,734, entitled "ROTATIONAL ATHERECTOMY DEVICE WITH RADIALLY EXPANDABLE PRIME MOVER COUPLING"; U.S. Pat. No. 8,597,313, entitled "ECCENTRIC ABRADING HEAD FOR HIGH-SPEED ROTATIONAL ATHERECTOMY DEVICES"; U.S. Pat. No. 8,439,937, entitled "SYSTEM, APPARATUS AND METHOD FOR OPENING AN OCCLUDED LESION"; U.S. Pat. Pub. No. 2009/0299392, entitled "ECCENTRIC ABRADING ELEMENT FOR HIGH-SPEED ROTATIONAL ATHERECTOMY DEVICES"; U.S. Pat. Pub. No. 2010/0198239, entitled "MULTI-MATERIAL ABRADING HEAD FOR ATHERECTOMY DEVICES HAVING LATERALLY DISPLACED CENTER OF MASS"; U.S. Pat. Pub. No. 2010/0036402, entitled "ROTATIONAL ATHERECTOMY DEVICE WITH PRE-CURVED DRIVE SHAFT"; U.S. Pat. Pub. No. 2009/0299391, entitled "ECCENTRIC ABRADING AND CUTTING HEAD FOR HIGH-SPEED ROTATIONAL ATHERECTOMY DEVICES"; U.S. Pat. Pub. No. 2010/0100110, entitled "ECCENTRIC ABRADING AND CUTTING HEAD FOR HIGH-SPEED ROTATIONAL ATHERECTOMY DEVICES"; U.S. Design Pat. No. D610,258, entitled "ROTATIONAL ATHERECTOMY ABRASIVE CROWN"; U.S. Design Pat. No. D6,107,102, entitled "ROTATIONAL ATHERECTOMY ABRASIVE CROWN"; U.S. Pat. Pub. No. 2009/0306689, entitled "BIDIRECTIONAL EXPANDABLE HEAD FOR ROTATIONAL ATHERECTOMY DEVICE"; U.S. Pat. Pub. No. 2010/0211088, entitled "ROTATIONAL ATHERECTOMY SEGMENTED ABRADING HEAD AND METHOD TO IMPROVE ABRADING EFFICIENCY"; U.S. Pat. Pub. No. 2013/0018398, entitled "ROTATIONAL ATHERECTOMY DEVICE WITH ELECTRIC MOTOR"; and U.S. Pat. No. 7,666,202, entitled "ORBITAL ATHERECTOMY DEVICE GUIDE WIRE DESIGN." It is contemplated by this invention that the features of one or more of the embodiments of the present invention may be combined with one or more features of the embodiments of atherectomy devices described therein.

A "therapeutic agent" comprises any substance capable of exerting an effect including, but not limited to therapeutic, prophylactic or diagnostic. Thus, therapeutic agents may comprise anti-inflammatories, anti-infectives, analgesics, anti-proliferatives, and the like including but not limited to antirestenosis drugs. Therapeutic agent further comprises mammalian stem cells. Therapeutic agent as used herein further includes other drugs, genetic materials and biological materials. The genetic materials mean DNA or RNA, including, without limitation, of DNA/RNA encoding a useful protein, intended to be inserted into a human body including viral vectors and non-viral vectors. Viral vectors include adenoviruses, gutted adenoviruses, adeno-associated virus, retroviruses, alpha virus, lentiviruses, herpes simplex virus, ex vivo modified cells (e.g., stem cells, fibroblasts, myoblasts, satellite cells, pericytes, cardiomyocytes, skeletal myocytes, macrophage), replication competent viruses, and hybrid vectors. Non-viral vectors include artificial chromosomes and mini-chromosomes, plasmid DNA vectors, cationic polymers, graft copolymers, neutral polymers PVP, SP1017, lipids or lipoplexes, nanoparticles and microparticles with and without targeting sequences such as the protein transduction domain (PTD). The biological materials include cells, yeasts, bacteria, proteins, peptides, cytokines and hormones. Examples for peptides and proteins include growth factors (FGF, FGF-1, FGF-2, VEGF, Endothelial Mitogenic Growth Factors, and epidermal growth factors, transforming growth factor .alpha. and .beta., platelet derived endothelial growth factor, platelet derived growth factor, tumor necrosis factor .alpha., hepatocyte growth factor and insulin like growth factor), transcription factors, proteinkinases, CD inhibitors, thymidine kinase, and bone morphogenic proteins. These dimeric proteins can be provided as homodimers, heterodimers, or combinations thereof, alone or together with other molecules.

"Therapeutic agent" further includes cells that can be of human origin (autologous or allogeneic) or from an animal source (xenogeneic), genetically engineered, if desired, to deliver proteins of interest at the transplant site. Cells within the definition of therapeutic agents herein further include whole bone marrow, bone marrow derived mono-nuclear cells, progenitor cells (e.g., endothelial progenitor cells) stem cells (e.g., mesenchymal, hematopoietic, neuronal), pluripotent stem cells, fibroblasts, macrophage, and satellite cells.

"Therapeutic agent" also includes non-genetic substances, such as: anti-thrombogenic agents such as heparin, heparin derivatives, and urokinase; anti-proliferative agents such as enoxaprin, angiopeptin, or monoclonal antibodies capable of blocking smooth muscle cell proliferation, hirudin, and acetylsalicylic acid, amlodipine and doxazosin; anti-inflammatory agents such as glucocorticoids, betamethasone, dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, taxol and its analogs or derivatives; anesthetic agents such as lidocaine, bupivacaine, and ropivacaine; anti-coagulants such as heparin, antithrombin compounds, platelet receptor antagonists, anti-thrombin antibodies, anti-platelet receptor antibodies, aspirin, dipyridamole, protamine, hirudin, prostaglandin inhibitors, platelet inhibitors and tick antiplatelet peptides; vascular cell growth promoters such as growth factors, Vascular Endothelial Growth Factors, growth factor receptors, transcriptional activators, and translational promoters; vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms; anti-oxidants, such as probucol; antibiotic agents, such as penicillin, cefoxitin, oxacillin, tobranycin angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme, inhibitors including captopril and enalopril. The biologically active material can be used with (a) biologically non-active material(s) including a solvent, a carrier or an excipient, such as sucrose acetate isobutyrate, ethanol, n-methyl pymolidone, dimethyl sulfoxide, benzyl benxoate and benzyl acetate.

Further, "therapeutic agent" includes, in particular in a preferred therapeutic method of the present invention comprising the administration of at least one therapeutic agent to a procedurally traumatized, e.g., by an angioplasty or atherectomy procedure, mammalian vessel to inhibit restenosis. Preferably, the therapeutic agent is a cytoskeletal inhibitor or a smooth muscle inhibitor, including, for example, taxol and functional analogs, equivalents or derivatives thereof such as taxotere, paclitaxel, Abraxane™, Coroxane™ or a cytochalasin, such as cytochalasin B, cytochalasin C, cytochalasin A, cytochalasin D, or analogs or derivatives thereof.

Additional specific examples of "therapeutic agents" that may be applied to a bodily lumen using various embodiments of the present invention comprise, without limitation:

L-Arginine;
Adipose Cells;

Genetically altered cells, e.g., seeding of autologous endothelial cells transfected with the beta-galactosidase gene upon an injured arterial surface;

Erythromycin;
Penicillin;
Heparin;
Aspirin;
Hydrocortisone;
Dexamethasone;
Forskolin;
GP IIb-IIIa inhibitors;
Cyclohexane;
Rho Kinsase Inhibitors;
Rapamycin;
Histamine;
Nitroglycerin;
Vitamin E;
Vitamin C;
Stem Cells;
Growth Hormones;
Hirudin;
Hirulog;
Argatroban;
Vapirprost;
Prostacyclin;
Dextran;
Erythropoietin;
Endothelial Growth Factor;
Epidermal Growth Factor;
Core Binding Factor A;
Vascular Endothelial Growth Factor;
Fibroblast Growth Factors;
Thrombin;
Thrombin inhibitor; and
Glucosamine, among many other therapeutic substances.

The therapeutic agent delivery system of the present invention may be used to apply the therapeutic agent to any surface of a body lumen where a catheter can be inserted and wherein the body lumen or conduit comprises a diameter that is larger than the diameter of the catheter. Such body lumen includes, inter alia, blood vessels, urinary tract, coronary vasculature, esophagus, trachea, colon, and biliary tract.

Figure 1B:
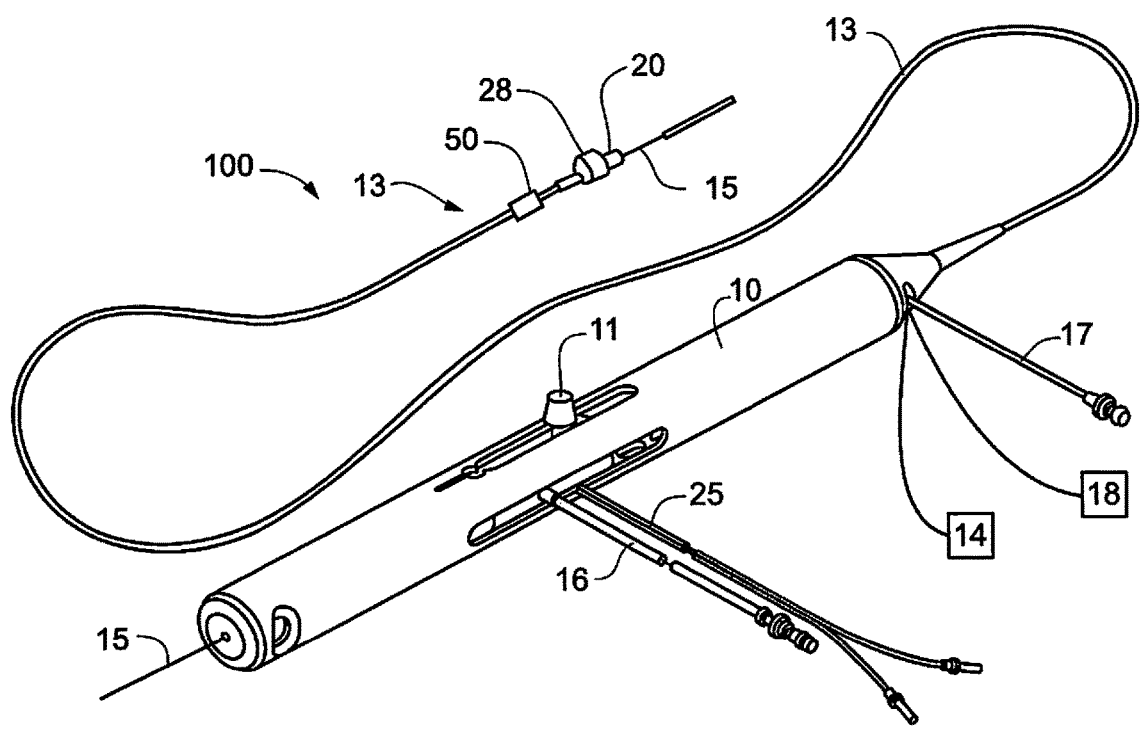
FIG. 1B illustrates a perspective view of one embodiment of the present invention.

Turning now to FIGS. 1A and 1B, embodiments of a rotational atherectomy device 100 according to the present invention are illustrated. The device of FIG. 1B includes a handle portion 10, an elongated, flexible drive shaft 20 having an abrading head 28 attached thereto and an elongated catheter 13 extending distally from the handle portion 10 with a lumen therethrough arranged for receiving the drive shaft 20. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13. FIG. 1A differs from the system of FIG. 1B in that there is no drive shaft 20 or abrading head 28 to illustrate that therapeutic agent infusion system 50 may be used alone, or as an adjunctive treatment following, e.g., a rotational atherectomy procedure and/or angioplasty and/or stenting.

The handle 10 desirably contains an electric motor (or other rotational drive mechanism, e.g., a turbine) for rotating the drive shaft 20 at high speeds. The handle 10 typically may be connected to a power source, such as compressed air delivered through a tube 16 if a turbine is used or an electrical outlet if an electric motor is provided. A pair of fiber optic cables 25, alternatively a single fiber optic cable may be used, may also be provided for monitoring the speed of rotation of the turbine and drive shaft 20. The handle 10 also desirably includes a control knob 11 for advancing and retracting the turbine and drive shaft 20 with respect to the catheter 13 and the body of the handle 10.

Both embodiments shown in FIGS. 1A and 1B comprise a therapeutic agent infusion system 50 disposed on catheter 13, an air source 14 in fluid communication with therapeutic agent infusion system 50 and a therapeutic agent or drug reservoir 18 in fluid communication with therapeutic agent infusion system 50. Therapeutic agents or drugs in reservoir 18 are microencapsulated within a capsule that is well known in the art so that the therapeutic agents or drugs are enclosed in microscopic particles by formation of thin coatings of wall material around the substances. As described above, microencapsulation has a number of benefits that the present invention takes advantage of.

Figure 2A:
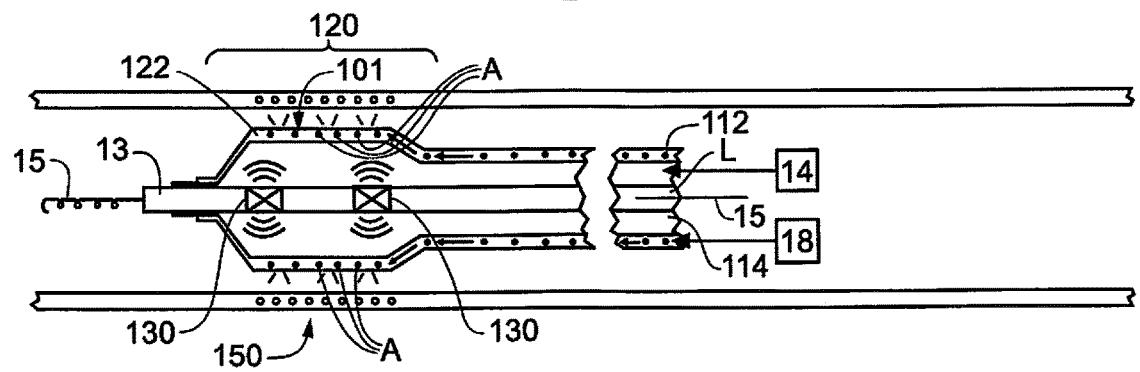
FIG. 2A illustrates a side cutaway view of one embodiment of the present invention.
Figure 2B:
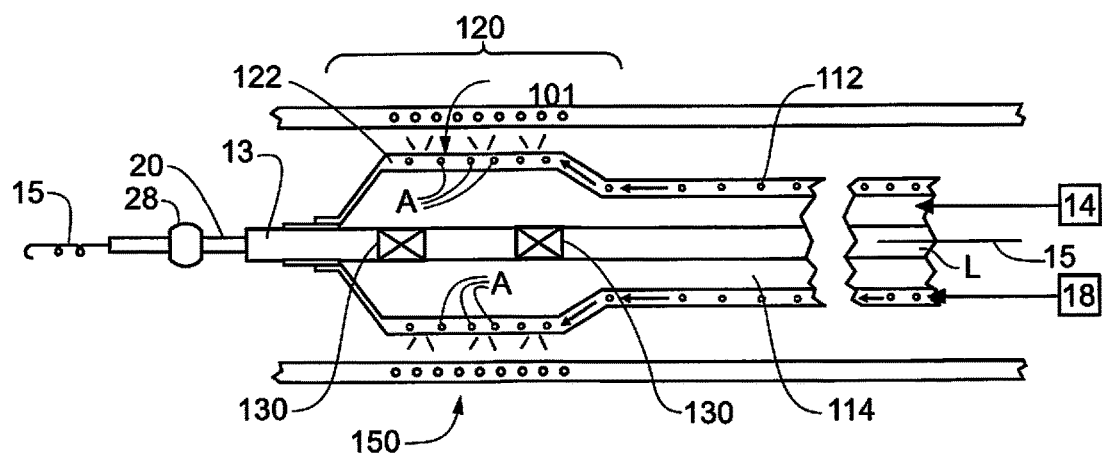
FIG. 2B illustrates a side cutaway view of one embodiment of the present invention.

A specific embodiment of the therapeutic agent infusion system 50, represented as 150 and 150' respectively, is provided in FIGS. 2A and 2B. The primary difference between these figures is the presence of the rotational drive shaft 2A and abrading head 28 attached thereto in FIG. 2B.

An inflatable balloon 100 is provided with a drug infusion lumen 112 in fluid connection with the therapeutic agent reservoir 18 as well as a balloon inflation lumen 114 in fluid connection with the air source 14. Balloon 101 is attached to catheter 13, with guide wire 15 received within catheter lumen L in FIG. 2A, and within the lumen of the drive shaft 20 in FIG. 2B wherein the drive shaft 20 is received within catheter lumen L. Balloon 101 comprises an inflatable section 120 which further comprises an intermediate section 122 that has apertures A therethrough and in fluid communication with the drug infusion lumen 112. Apertures A enable the encapsulated therapeutic agent to be pushed from the therapeutic agent reservoir 18 which may or may not comprise a pumping mechanism, such as a pump or other pressure generating means such as and without limitation a syringe, through the drug infusion lumen 112 and outwardly through apertures A to contact the conduit or vessel wall in the region of interest.

To encourage the encapsulated therapeutic agent(s) to be delivered into the conduit or vessel wall, at least one, and preferably two, ultrasound transducer(s) is attached on the catheter 13 and generally within the inflatable section 120 of balloon 102, with more preferred location within the intermediate section 122 of balloon 102. The ultrasonic energy generated by the transducer(s) 130, delivered generally in an outward radial direction—directed away from the longitudinal axis of the catheter 13—provides for sonoporation, a process that increases the uptake of the specific agent(s) being delivered to the conduit or vessel wall by causing the microbubble encapsulating the therapeutic agent(s) to vibrate which when in contact with the conduit or vessel wall, in turn, causes (1) pore formation in the wall surface; (2) endocytosis; and/or (3) openings in the cell-cell junctions in the wall. All of these processes make it easier for the encapsulated agent(s) to enter the wall and cells within the wall. When the microbubble encapsulating the agent(s) bursts due to ultrasonic forces, the agent(s) is released therefrom and may then be delivered to the wall and/or cells therein. If the microbubbles are not taken up by the wall or wall cells and do not burst, they are simply eliminated through normal bodily processes without impacting non-target organs.

Figure 3A:
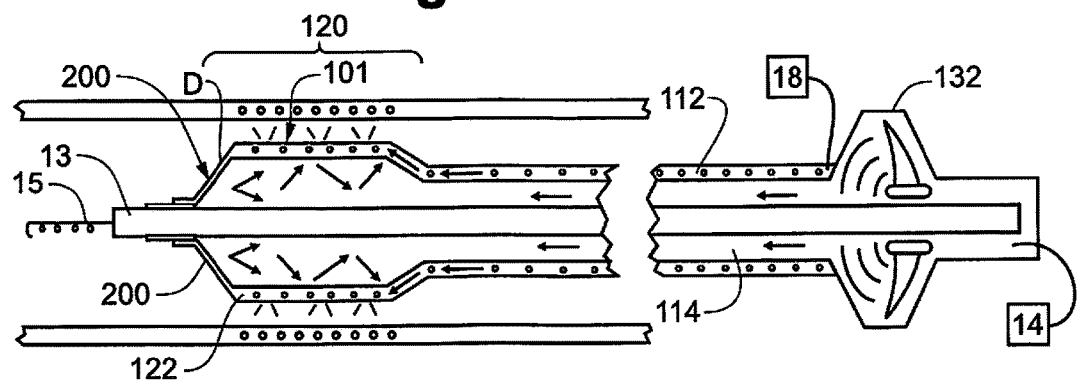
FIG. 3A illustrates a side cutaway view of one embodiment of the present invention.
Figure 3B:
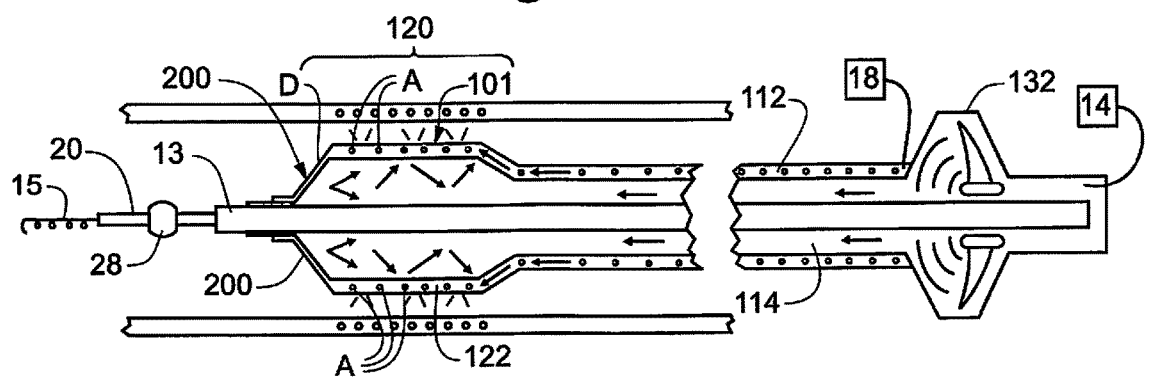
FIG. 3B illustrates a side cutaway view of one embodiment of the present invention.

Turning now to FIGS. 3A and 3B, an alternate embodiment 250, 250' of the therapeutic infusion system 50 is illustrated. FIG. 3B differs from FIG. 3A in that a drive shaft 20 with abrading head 28 thereon is disposed within catheter 13, wherein guide wire 15 is received within drive shaft 20 lumen. FIG. 3A comprises the guide wire 15 disposed and received within the lumen L of catheter 13.

The remaining elements of FIGS. 3A and 3B, with the exception of the function and placement of the ultrasound elements are the same as described in connection with FIGS. 2A and 2B, including but not limited to apertures A along intermediate section 122 with some new and modified elements as will now be described. Instead of placing the ultrasound transducer(s) within the inflatable section 120 on catheter 13 as in FIGS. 2A and 2B, the embodiments of FIGS. 3A and 3B provide at least one transducer 132 and preferably two transducers 132 disposed on catheter 13 at a point that is proximal to balloon 101, i.e., in a direction closer to the operating handle 10. Transducer(s) 132 are arranged so that the ultrasonic energy waves are in fluid communication with the balloon infusion lumen 114. The ultrasonic waves generated by transducer(s) 132 are directed to travel distally along balloon infusion lumen 114 and into the inflatable section 120 of balloon 101 until reaching the distal end D of inflatable section 120. A reflector 200 is disposed on the inner surface of the distal end D of inflatable section 120, acting as a reflective surface for the incoming ultrasonic energy waves. The reflected waves, shown as arrows in FIGS. 3A and 3B will engage and energize the microbubbles encapsulating the therapeutic agent(s) and initiate the process of sonoporation as described above.

Figure 4A:
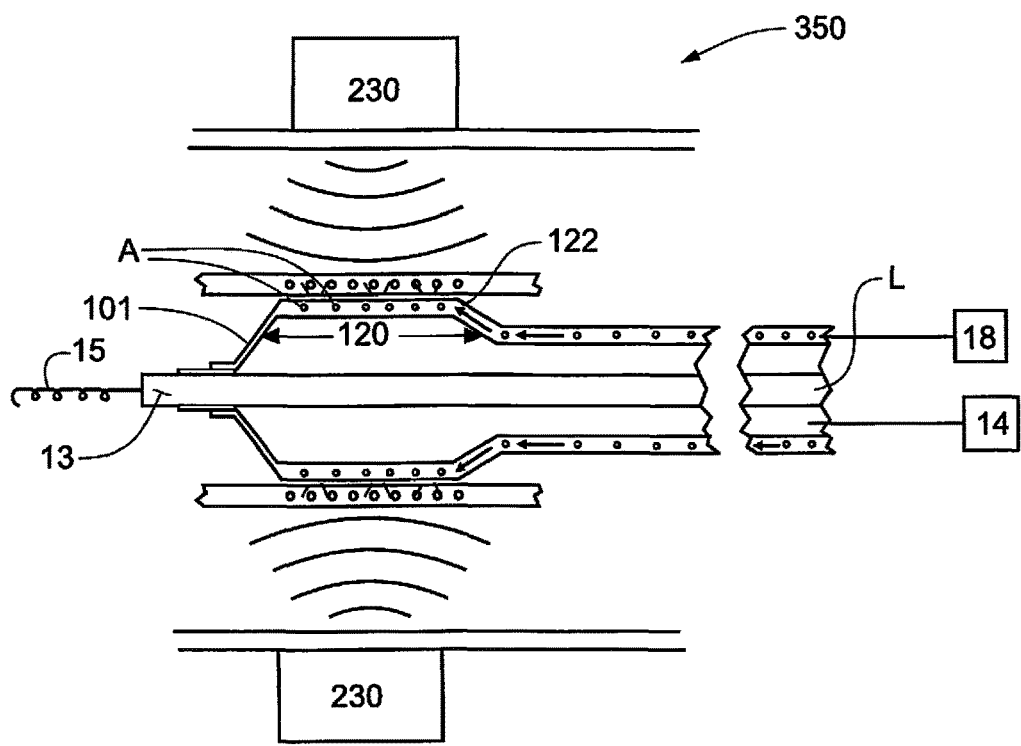
FIG. 4A illustrates a side cutaway view of one embodiment of the present invention.
Figure 4B:
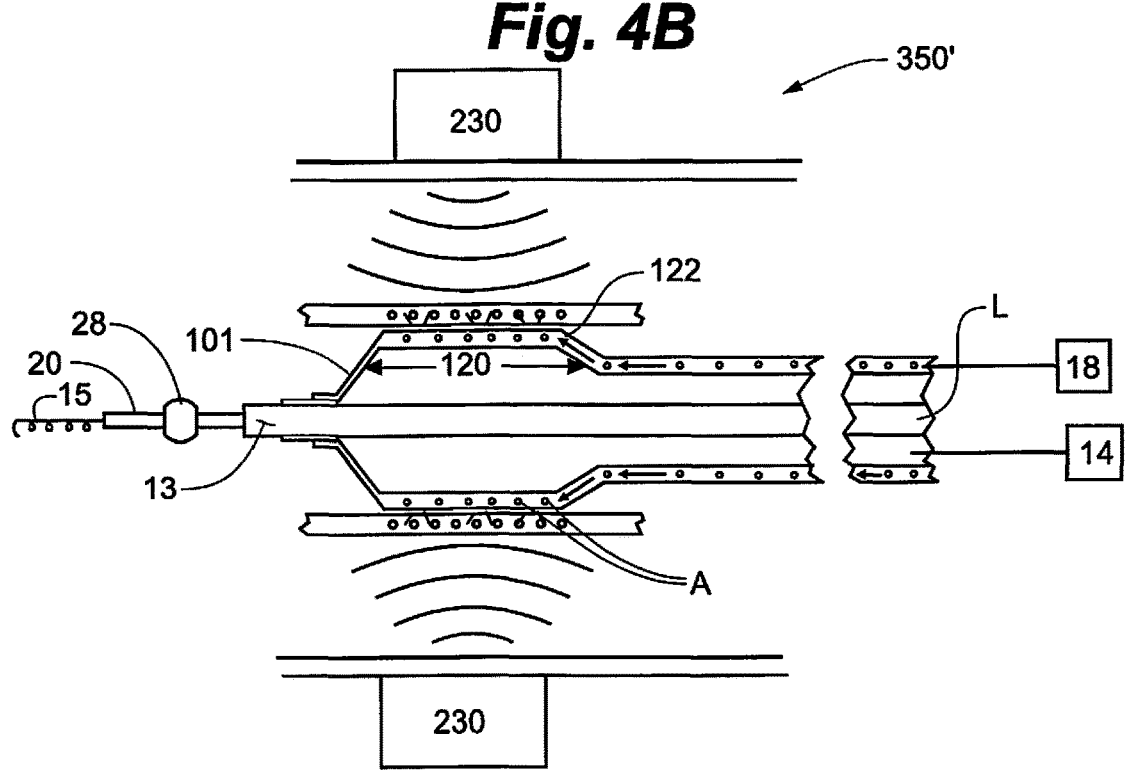
FIG. 4B illustrates a side cutaway view of one embodiment of the present invention.

FIGS. 4A and 4B similarly illustrate an ultrasonic enhancement, with the only differences between the Figures being the presence of drive shaft 20 with abrading head 28 attached thereto and the guide wire 15 received within the drive shaft 20 lumen in FIG. 4B instead of the guide wire 15 being received within the catheter lumen L as in FIG. 4A. Therapeutic reservoir 18 is in fluid communication with drug infusion lumen 112 and air supply 14 in fluid communication with balloon inflation lumen 114 as in previous figures. Balloon 101 comprises an inflatable section 120, with an intermediate section 122 having apertures A therethrough as in previously described embodiments in FIGS. 2A, 2B, 3A and 3B.

At least one, preferably two ultrasonic transducer(s) 230 are provided in contact with the patient's skin directly above and/or below the inflatable section 120 of balloon 101. In this embodiment, the ultrasonic energy waves are generated by the transducer(s) 230 and are directed in an inwardly radiating direction toward the intermediate section 122 and the conduit or vessel wall's treatment area corresponding with the location of intermediate section 122, thereby entering the conduit or vessel wall from an external direction and initiating the sonoporation process as described earlier to encourage uptake of the microencapsulated agent(s) and delivery of the agent(s) by bursting the microbubble encapsulating the agent(s) when within the wall and/or cells within the wall.

Figure 5A:
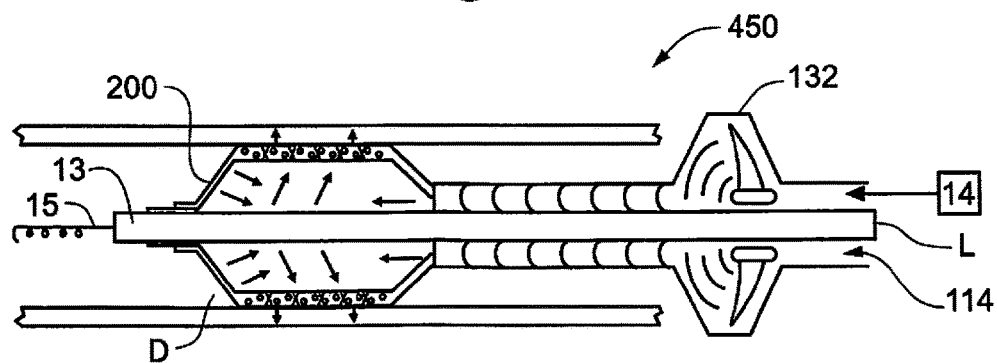
FIG. 5A illustrates a side cutaway view of one embodiment of the present invention.
Figure 5B:
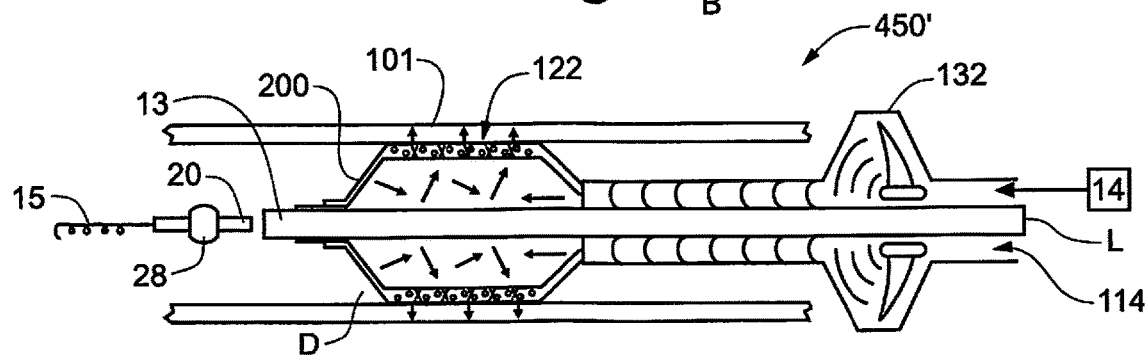
FIG. 5B illustrates a side cutaway view of one embodiment of the present invention.

FIGS. 5A and 5B illustrate therapeutic infusion systems 450 and 450' comprising a slight variation to the embodiments of FIGS. 3A and 3B in that the microencapsulated therapeutic agent(s) are not initially within a drug infusion lumen, but instead are coated onto the exterior surface of the intermediate section 122 of balloon 101. As a result, there is no need for a drug infusion lumen. In this case, initiation of the ultrasound transducer(s) 132 directs ultrasonic energy waves distally toward the balloon 101 along balloon infusion lumen 114 and ultimately reflected by reflector 200 disposed on the internal surface of the distal end of balloon 101. When balloon 101 is inflated against the conduit or vessel wall, pressing the microencapsulated agent(s) against the wall, the reflected ultrasonic energy waves energize the microbubbles and initiate the sonoporation process described above, enhancing the uptake of the microbubbles and the ultimate delivery of the encapsulated agent within the wall and/or cells therein when the microbubble bursts.

Figure 6A:
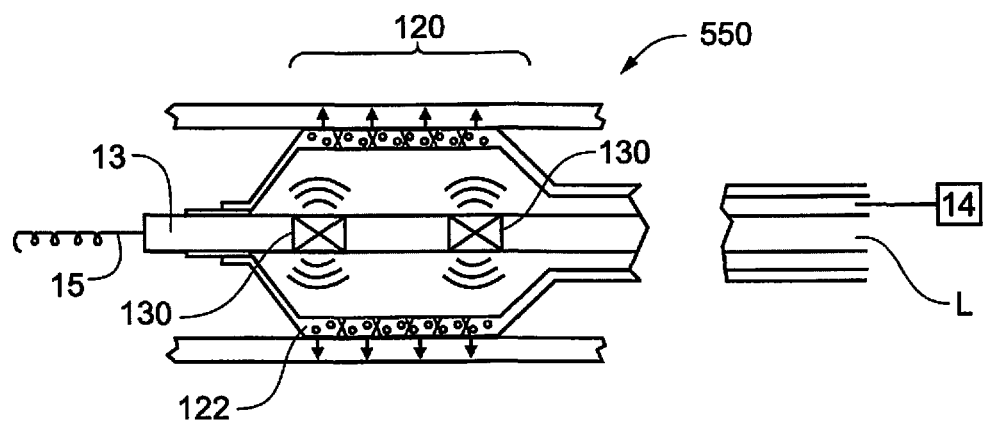
FIG. 6A illustrates a side cutaway view of one embodiment of the present invention.
Figure 6B:
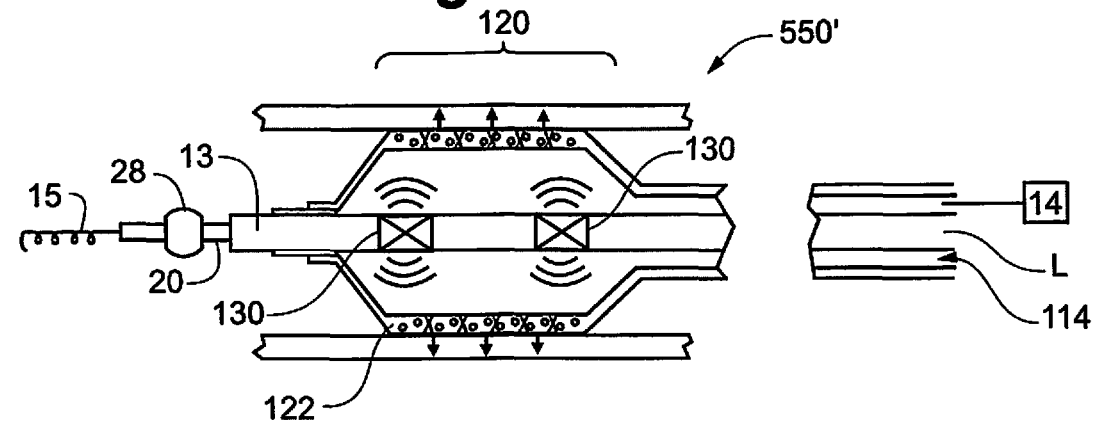
FIG. 6B illustrates a side cutaway view of one embodiment of the present invention.

The therapeutic infusion system 550, 550' of FIGS. 6A and 6B are identical with those described in connection with FIGS. 2A and 2B except that, as in FIGS. 5A and 5B, the microencapsulated therapeutic agent(s) are coated onto the exterior surface of the intermediate section 122 of balloon 101 and, as a result, there is no need for a drug reservoir 18 or a drug infusion lumen 114.

In this case, initiation of the ultrasound transducer(s) 130 disposed on catheter 13 within the inflatable section 120 of balloon 101 directs ultrasonic energy waves outwardly radially toward the intermediate section 122 of balloon 101 and the microencapsulated agent(s) coated thereon. When balloon 101 is inflated against the conduit or vessel wall, pressing the microencapsulated agent(s) against the wall, the reflected ultrasonic energy waves energize the microbubbles and initiate the sonoporation process described above, enhancing the uptake of the microbubbles and the ultimate delivery of the encapsulated agent within the wall and/or cells therein when the microbubble bursts.

FIGS. 7 and 8 illustrate a slightly different approach to an alternate embodiment of a therapeutic infusion system 50. As illustrated, balloon 650 comprises an inflatable portion 120 and an occlusion portion 150 attached to catheter 13, wherein the inflatable portion 120 and the occlusion portion 150 are inflatable and each in fluid communication with the balloon inflation lumen 112 and with air source 14.

As illustrated in FIG. 8, and as previously described, guide wire 15 is received within catheter lumen L. As with previously described embodiments, a drive shaft 20 and abrading head 28 disposed thereon may be alternatively received within catheter lumen L and the guide wire 15 received with the lumen of drive shaft 20.

Further, in the illustrated case, microencapsulated therapeutic agent(s) are stored in reservoir 18, and are flowed distally, with optional pump or other fluid pressure generating means such as, without limitation, a syringe, therefrom along drug infusion lumen 112 in a distal direction and toward balloon's inflatable section 120 and intermediate section 122 where a plurality of apertures A are provided through balloon's wall and are in fluid communication with the drug infusion lumen 112.

An alternate embodiment in the cases of FIGS. 7 and 8 may comprise the therapeutic agents being not encapsulated, as no ultrasonic energy is being supplied or is required. However, microencapsulation is still a preferred embodiment as a mechanism to prevent exposure of the patient's system and non-target organs to the therapeutic agent(s).

It is understood that an alternate embodiment may further comprise, as in FIGS. 6A and 6B, the microencapsulated therapeutic agent(s) being coated on the exterior of the intermediate section 122. In this case, no drug delivery lumen 112, pumping mechanism, or reservoir 18 are required.

In the illustrated case, occlusion portion 150 is disposed distal to inflatable portion 120 and used to stop blood flow during the drug infusion process. As the skilled artisan will recognize, inclusion portion 150 may be entirely absent and within the inventive scope. Alternatively, there may be another occlusion portion 150 positioned on the proximal side of inflatable portion 120 so that at least one occlusion portion 150 is within the scope of the invention.

As seen in FIGS. 7 and 8, a pulse generator 500 is provided in communication with drug reservoir 18, diaphragm D and operating handle 10. Pulse generator 500 is arranged to provide a pulsing energy at a selectable frequency to drive the diaphragm D in order to enhance the uptake of the microencapsulated therapeutic agent(s). In this manner, the therapeutic agent(s) in the drug reservoir 18, the drug infusion lumen 112—including those agents in the drug infusion lumen 112 in the intermediate section 122 of balloon's inflatable section 120 and, therefore, in proximity with apertures A, will be urged in the pulsing frequency distally to and through apertures A until a therapeutic amount of the therapeutic agent is administered to the conduit or vessel wall.

In certain embodiments, an EKG monitor 502 may be provided in contact with the patient and with operating handle 10 and pulse generator 500 in order to synchronize the patient's blood pulses with the energy pulses generated by pulse generator 500. EKG monitor 502 is optional and is therefore shown with a dashed line connection to pulse generator 500. Alternatively, a range of frequencies may be developed for a certain population of individuals or for an individual, e.g., the specific patient. The goal in this case is to induce the tissue and cells therein of the conduit or vessel wall in the treatment into a natural rhythm that matches the patient's actual or likely blood pressure. In this manner, the cells are experiencing the same mechanical and/or biological forces that a healthy, non-occluded, conduit or vessel may experience, and thereby promoting higher efficiency of uptake.

Alternatively, it may be useful to increase the pulsing energy frequency generated with the pulse generator 500 to match those of a certain population of individuals or a specific individual, e.g., the patient, at maximum cardiac output, or even higher. Such an approach may work to lessen the treatment time as more agent(s) is taken up by the wall and cells therein in less time.

As will be well understood in the art, a disposable diaphragm D in connection with the pulse generator 500 and the therapeutic agent(s) in the reservoir 18 and drug infusion lumen 112 will be used to deliver the energy pulses to the therapeutic agent.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

The invention claimed is:

1. A system for enhancing the efficiency of administering therapeutic agents and delivering a therapeutically effective amount of the therapeutic agent to the wall of a biological conduit in a treatment region of interest of a patient, the biological conduit having a diameter, comprising:
   a catheter inserted at least partially within the biological conduit and comprising a lumen;
   an inflatable balloon attached proximate a distal end of the catheter and comprising
   an inflatable portion, and
   an intermediate section in the inflatable portion and comprising a plurality of apertures therethrough;
   a therapeutic agent infusion lumen in fluid communication with the plurality of apertures;
   a therapeutic agent reservoir located outside the patient's body, comprising therapeutic agent therein, the therapeutic agent within the therapeutic agent reservoir in fluid communication with the therapeutic agent infusion lumen;
   a balloon infusion lumen in fluid communication with the inflatable balloon, wherein the balloon infusion lumen and therapeutic agent infusion lumen are not in fluid communication with each other;
   a therapeutic agent pumping mechanism located outside the patient's body and in fluid communication with the therapeutic agent reservoir, the therapeutic agent infusion lumen and the apertures, but not in fluid communication with the balloon infusion lumen; and
   a pulse generator located outside the patient's body and in operative communication with the therapeutic agent pumping mechanism and further adapted to generate a range of therapeutically effective frequencies to the therapeutic agent to drive the therapeutic agent through the therapeutic agent infusion lumen and out of the plurality of apertures of the inflatable balloon in response to pulses generated by the therapeutic agent pulse generator that correspond with the generated therapeutically effective frequencies.

2. The system of claim 1, further comprising an occlusion balloon in fluid communication with the balloon infusion lumen and located distally to the inflatable portion.

3. The system of claim 2, further comprising an occlusion portion in fluid communication with the balloon infusion lumen and located proximally to the inflatable portion.

4. The system of claim 1, further comprising:
   an EKG monitor in operative communication with the patient and with the pulse generator and capable of measuring the blood pulse of the patient.

5. The system of claim 3, further comprising:
   an EKG monitor in operative communication with the patient and with the pulse generator.

6. The system of claim 1, wherein the range of therapeutically effective frequencies generated match a blood pulse frequency of the patient.

7. The system of claim 5, wherein the range of therapeutically effective frequencies generated match the blood pulse frequency measured by the EKG monitor.

* * * * *